(12) United States Patent
Yamazaki et al.

(10) Patent No.: US 9,869,821 B2
(45) Date of Patent: Jan. 16, 2018

(54) PROBE FOR OPTICAL IMAGING

(71) Applicant: NAMIKI SEIMITSU HOUSEKI KABUSHIKI KAISHA, Tokyo (JP)

(72) Inventors: Hiroshi Yamazaki, Kuroishi (JP); Eri Fukushima, Kuroishi (JP); Tomoyuki Kugo, Kuroishi (JP); Norikazu Sato, Kuroishi (JP); Takayuki Koshikawa, Kuroishi (JP); Chihiro Okamoto, Kuroishi (JP); Takafumi Asada, Kuroishi (JP)

(73) Assignee: Namiki Seimitsu Houseki Kabushiki Kaisha, Tokyo (JP)

( * ) Notice: Subject to any disclaimer, the term of this patent is extended or adjusted under 35 U.S.C. 154(b) by 99 days.

(21) Appl. No.: 15/093,381

(22) Filed: Apr. 7, 2016

(65) Prior Publication Data

US 2016/0223754 A1 Aug. 4, 2016

Related U.S. Application Data

(63) Continuation of application No. PCT/JP2014/084003, filed on Dec. 23, 2014.

(30) Foreign Application Priority Data

Jan. 6, 2014 (JP) ................. 2014-000642

(51) Int. Cl.
G02B 6/26 (2006.01)
G02B 6/36 (2006.01)
(Continued)

(52) U.S. Cl.
CPC .......... *G02B 6/3624* (2013.01); *A61B 5/0066* (2013.01); *A61B 5/0084* (2013.01);
(Continued)

(58) Field of Classification Search
CPC .................................................. A61B 5/0066
See application file for complete search history.

(56) References Cited

U.S. PATENT DOCUMENTS

| 5,240,003 A * | 8/1993 | Lancee ..................... A61B 8/12 310/162 |
| 6,687,010 B1 * | 2/2004 | Horii .................... G01B 9/0201 356/479 |
| 8,861,900 B2 * | 10/2014 | Bhagavatula ........ A61B 5/0066 385/12 |
| 8,967,885 B2 * | 3/2015 | Bhagavatula ........ G02B 6/2552 385/93 |

(Continued)

FOREIGN PATENT DOCUMENTS

| JP | 3885114 B2 | 2/2007 |
| JP | 4461216 B2 | 5/2010 |

(Continued)

OTHER PUBLICATIONS

International Search Report issued in PCT/JP2014/084003; dated Mar. 31, 2015.

*Primary Examiner* — Sung Pak
(74) *Attorney, Agent, or Firm* — Studebaker & Brackett PC

(57) ABSTRACT

A 3D-scanning optical imaging probe which inhibits rotation unevenness of rotational sections, shaft run-out, friction, and rotation transmission delay by reducing the occurrence of torque loss and rotation transmission delay, and which is capable of obtaining 3D scans and observation images within a fixed frontal range. A substantially tubular catheter has, provided along substantially the same line therein: a fixed-side optical fiber; a first optical path conversion means which is rotationally driven by a first motor, and which rotates and emits a beam of light forwards and tilted at an angle with respect to a rotational axis; and a second optical path conversion means which, at a tip side of a rotation-side optical fiber rotationally driven by a second motor, tilts an optical path by a micro-angle with respect to the rotational axis, and rotates and emits the beam of light to irradiate the first optical path conversion means therewith.

8 Claims, 15 Drawing Sheets

(51) Int. Cl.
*G02B 23/26* (2006.01)
*G02B 26/08* (2006.01)
*G02B 26/10* (2006.01)
*G03B 15/03* (2006.01)
*G03B 35/00* (2006.01)
*G03B 37/00* (2006.01)
*A61B 5/00* (2006.01)

(52) U.S. Cl.
CPC ........... *G02B 6/3604* (2013.01); *G02B 23/26* (2013.01); *G02B 26/0883* (2013.01); *G02B 26/108* (2013.01); *G03B 15/03* (2013.01); *G03B 35/00* (2013.01); *G03B 37/005* (2013.01)

(56) References Cited

U.S. PATENT DOCUMENTS

| | | | |
|---|---|---|---|
| 9,036,966 B2* | 5/2015 | Bhagavatula | ............ G02B 6/32 385/33 |
| 2005/0143664 A1* | 6/2005 | Chen | .................... A61B 5/6852 600/478 |
| 2009/0079993 A1 | 3/2009 | Yatagai et al. | |
| 2015/0355413 A1* | 12/2015 | Bhagavatula | ........ A61B 5/0066 385/26 |

FOREIGN PATENT DOCUMENTS

| | | |
|---|---|---|
| JP | 4520993 B2 | 8/2010 |
| JP | 2011-240155 | 12/2011 |
| JP | 2013-022414 A | 2/2013 |

\* cited by examiner

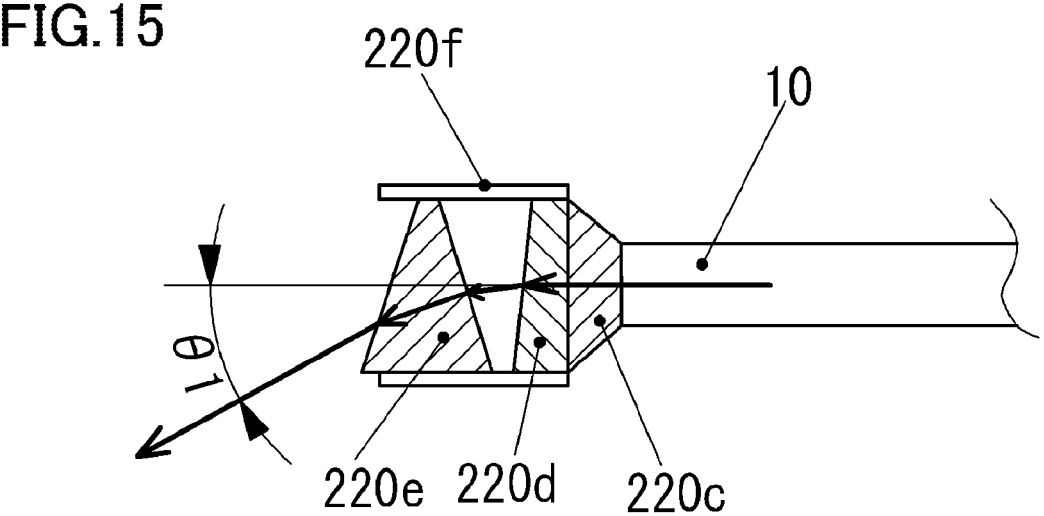

PROBE FOR OPTICAL IMAGING

TECHNICAL FIELD

The present invention relates to a probe for three-dimensional scanning optical imaging for three-dimensionally capturing and observing light reflected from a device under test in a mechanical device or the like.

BACKGROUND ART

Image diagnostic technologies (optical imaging technologies) are technologies widely used for mechanical devices and medical treatment fields. For example, in a manufacturing field of precision instruments, schemes such as X-ray computed tomography (CT) capable of capturing a tomographic image or a three-dimensional (3D) tomographic image, nuclear magnetic resonance, an optical coherence tomography (OCT) image using coherency of light, in addition to general camera observation and ultrasonic diagnostic equipment have been researched and used as means for an examination of an inner part of a deep hole and image diagnosis. In particular, referring to capturing of the tomographic image or the 3D tomographic image, the development of the OCT image diagnosis technology that obtains the most microscopic captured image has been recently drawing attention among the schemes.

The OCT image frequently uses far-red light having a wavelength of about 1,300 nanometers (nm) or a laser beam having a wavelength of about 400 nm as a light source, and each of the far-red light and the laser beam has a shorter wavelength than that of an ultrasonic wave, and thus is excellent in spatial resolving power. When a tomographic scheme is included in an endoscope, it is possible to achieve excellent spatial resolving power of about 10 micrometers (μm) or less [less than or equal to a ten of that of the ultrasonic diagnostic equipment].

In addition, the near infrared ray as a light source has non-invasiveness with respect to a living body. In particular, the near infrared ray is expected to be used to detect, diagnose, and treat a diseased part in a gastric region, a small intestine region, and a blood vessel part of an arterial flow or the like of a human body in the medical treatment field. For example, a representative configuration of an OCT endoscope to which this OCT image technology for mechanical devices and medical use is applied is as indicated in Patent Document 1.

Incidentally, in the OCT endoscope indicated in Patent Document 1, as illustrated in FIG. 8 of the document, a torque of a motor is delivered to a rotating shaft through a belt, and delivered to a lens unit through a flexible shaft which passes through an optical sheath having a shape of a tube and includes an optical fiber or the like. For this reason, in some cases, abrasion powder is generated due to friction between an inner peripheral surface of the optical sheath and the flexible shaft. In addition, rotation speed unevenness, rotation transmission delay, variation of torque loss, and the like have occurred due to friction, deflection, and torsion of the flexible shaft, elastic deformation of the belt, or the like. Thus, an obtained OCT analyzed image has been in disorder, and requested spatial resolving power has not been acquired. Further, even though a two-dimensional (2D) tomographic image illustrated in FIG. 26 of the document can be obtained using the configuration, a 3D image cannot be obtained using the configuration.

In addition, an OCT endoscope illustrated in Patent Document 2 corresponds to a 3D image system in which a catheter having a shape of a long and thin tube is inserted into a circular guide catheter illustrated in FIG. 1 of the document, an optically-connected optical fiber or core which is rotatable and slidable is included in the catheter, and the optical fiber is rotated and moved in a longitudinal direction as illustrated in FIG. 3 of the document to irradiate a body tissue, thereby observing an OCT analyzed image. However, this configuration has a problem in that abrasion powder is generated due to friction between the inner peripheral surface of the catheter and an outer peripheral surface of a drive shaft. In addition, rotation speed unevenness, rotation transmission delay, change of torque loss, and the like have occurred due to friction, deflection, and torsion of the drive shaft, and thus an obtained analyzed image has been in disorder, and requested spatial resolving power has not been acquired.

In addition, in the invention disclosed in Patent Document 3, a reflecting mirror is directly connected to a tip of a rotating shaft of a motor illustrated in FIG. 2 of the document. However, in this configuration, even though a 2D tomographic image can be obtained using the reflecting mirror which rotates, a 3D image cannot be obtained.

CITATION LIST

Patent Document

Patent Document 1: JP 3885114 B1
Patent Document 2: JP 4520993 B1
Patent Document 3: JP 4461216 B1

SUMMARY OF THE INVENTION

Problem to be Solved by the Invention

The invention has been conceived in view of the above conventional circumstances, and an object of the invention is to provide a probe for 3D scanning-type optical imaging which prevents rotational irregularity, axial runout, friction, rotation transmission delay of a rotation mechanism that rotates and emits a light ray by reducing occurrences of rotation transmission delay, torque loss, and the like, and can perform 3D scanning of a certain range in a forward direction in addition to a rotation direction to obtain a 3D observation image, thereby simultaneously solving the problems.

Means for Solving Problem

A means for solving the above-mentioned problems is a probe for optical imaging which guides light entering a tip side to a rear side. In the probe, a fixed side optical fiber non-rotatably disposed and incorporated in a substantially tube-shaped catheter, a first optical path conversion means disposed on a tip side of the fixed side optical fiber and driven and rotated by a first motor to rotate and emit a light ray forward with an angle tilted with respect to a rotation center, a rotation side optical fiber which is disposed between the fixed side optical fiber and the first optical path conversion means, optically connected by an optical rotary connector, and driven and rotated by a second motor, and a second optical path conversion means for rotating and emitting light to a tip side of the rotation side optical fiber by tilting an optical path by a minute angle with respect to a rotation center, and emitting a light ray toward the first optical path means are substantially collinearly disposed. An emission angle of a light ray is changed by controlling revolutions per minute of the two motors of the first optical path conversion means and the second optical path conversion means, and a high-resolution 3D observation image is obtained by emitting a light ray forward in a 3D region.

Effect of the Invention

According to the invention, occurrences of rotation transmission delay, torque loss, and the like are reduced without friction of an optical fiber in a catheter of an endoscope device, or the like. Further, when a first optical path conversion means and a second optical path conversion means independently rotate, a light ray is emitted forward in a 3D region. It is possible to obtain a 3D observation image having high spatial resolving power in an OCT endoscope that uses far-red light, a laser beam, or the like.

BRIEF DESCRIPTION OF DRAWINGS

FIG. 15 is a diagram for a description of a modified application example of the second optical path conversion means of the probe for optical imaging.

MODE(S) FOR CARRYING OUT THE INVENTION

Figure 1:
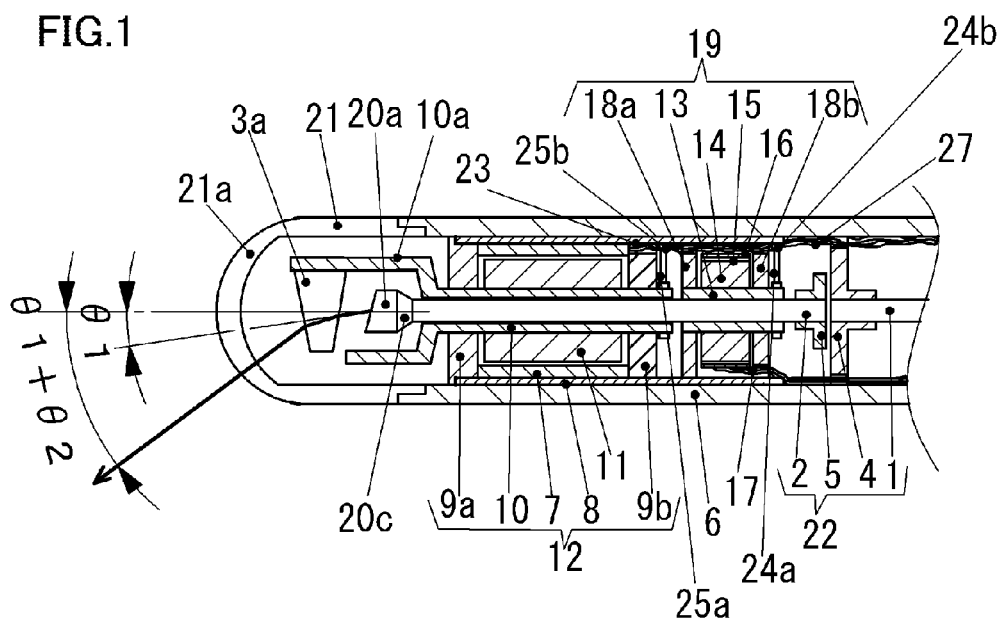
FIG. 1 is a cross-sectional view illustrating a probe for optical imaging according to a first embodiment of the invention.

According to a first characteristic of a probe for optical image of the present embodiment, a fixed side optical fiber non-rotatably disposed and incorporated in a substantially tube-shaped catheter, a first optical path conversion means disposed on a tip side of the fixed side optical fiber and driven and rotated by a first motor to rotate and emit a light ray forward at an angle inclined with respect to a rotation center, a rotation side optical fiber disposed between the fixed side optical fiber and the first optical path conversion means, optically connected by an optical rotary connector, and driven and rotated by a second motor, and a second optical path conversion means for rotating and emitting light to a tip side of the rotation side optical fiber by tilting an optical path by a minute angle with respect to a rotation center, and emitting a light ray toward the first optical path means are substantially collinearly disposed in a probe for optical imaging which guides light entering a tip side to a rear side, and the light ray is emitted forward by penetrating the optical rotary connector, the second optical path conversion means, and the first optical path conversion means in order from the fixed side optical fiber.

According to this configuration, occurrences of rotation transmission delay, torque loss, and the like are reduced without friction of an optical fiber in a catheter of an endoscope device or the like. Further, a light ray may be emitted forward in a 3D region by independently rotating the first optical path conversion means and the second optical path conversion means. Thus, it is possible to obtain a 3D observation image having high spatial resolving power in an OCT endoscope using far-red light, a laser beam, or the like.

According to a second characteristic, a rotating shaft of the first motor has a hollow shape, the first optical path conversion means is fixed to the rotating shaft, and the rotation side optical fiber rotatably penetrates into a hollow hole, and a rotating shaft of the second motor has a hollow shape, and the rotation side optical fiber is fixed to a hole corresponding to the hollow shape and rotated.

According to this configuration, the first motor and the second motor may be disposed behind the first optical path conversion means, and thus a light ray may be emitted forward without being disturbed by the motor or an electric wire of the motor. Therefore, 3D scanning may be performed forward in a wide range without shade.

According to a third characteristic, the first optical path conversion means is a rotatable prism.

According to this configuration, a light ray penetrates the first optical path conversion means, and 3D scanning may be performed forward in a wide range.

According to a fourth characteristic, the second optical path conversion means is a prism having a substantially inclined flat surface at a tip.

According to this configuration, a light ray is condensed by the second optical path conversion means and penetrates the means. Further, it is possible to rotate and emit light by inclining an optical path by a minute angle with respect to the rotation center.

According to a fifth characteristic, the probe further includes a first pulse generating means for generating at least one or more pulses per rotation according to a rotation angle of the first motor, a second pulse generating means for generating at least one or more pulses per rotation according to a rotation angle of the second motor, and a control means for adjusting rotation speeds of the first and the second motors by pulses from the first and second pulse generating means. The light ray is emitted forward from the first optical path conversion means at a rotation speed of N1 [rotations/second] by setting a relation between a rotation speed N1 of the first motor and a rotation speed N2 of the second motor to N2=N1−X [rotations/second], and an emission angle of the light ray with respect to the rotation center is changed at a speed of X [reciprocations/second].

According to this configuration, it is possible to emit a light ray forward in a wide range by a combination of rotation angles of the first optical path conversion means and the second optical path conversion means.

According to a sixth characteristic, a condensing lens, a first prism, and a second prism are substantially collinearly disposed in the second optical path conversion means.

According to this configuration, the second optical path conversion means may emit a light ray in a wide angle range.

According to a seventh characteristic, the rotatable prism and the substantially inclined flat surface at the tip of the prism of the second optical path conversion means are nonparallel to each other in the first optical path conversion means.

As they are disposed in nonparallel, attenuation of an optical path may be prevented, and an excellent high-resolution 3D image may be obtained.

According to an eighth characteristic, the second optical path conversion means is a prism having a substantially spherical surface inclined to the tip or a ball lens having a reflecting surface corresponding to a substantially flat surface in a portion of a substantially hemispheric shape.

According to this configuration, the device may be configured to be compact.

Next, a preferred embodiment of the invention will be described with reference to drawings.

Embodiment

A description will be given of an embodiment of a probe for 3D scanning-type optical imaging related to the invention.

Figure 2:
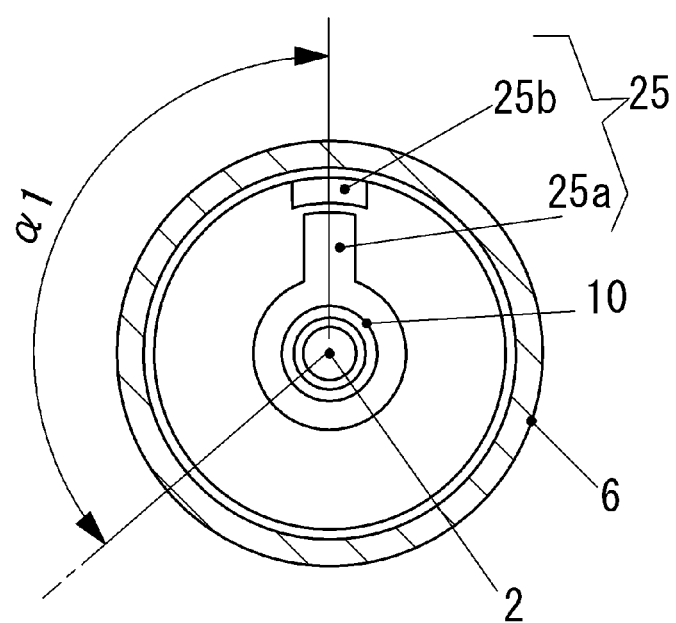
FIG. 2 is a diagram for a description of a pulse generator of a first motor of the probe for optical imaging.
Figure 3:
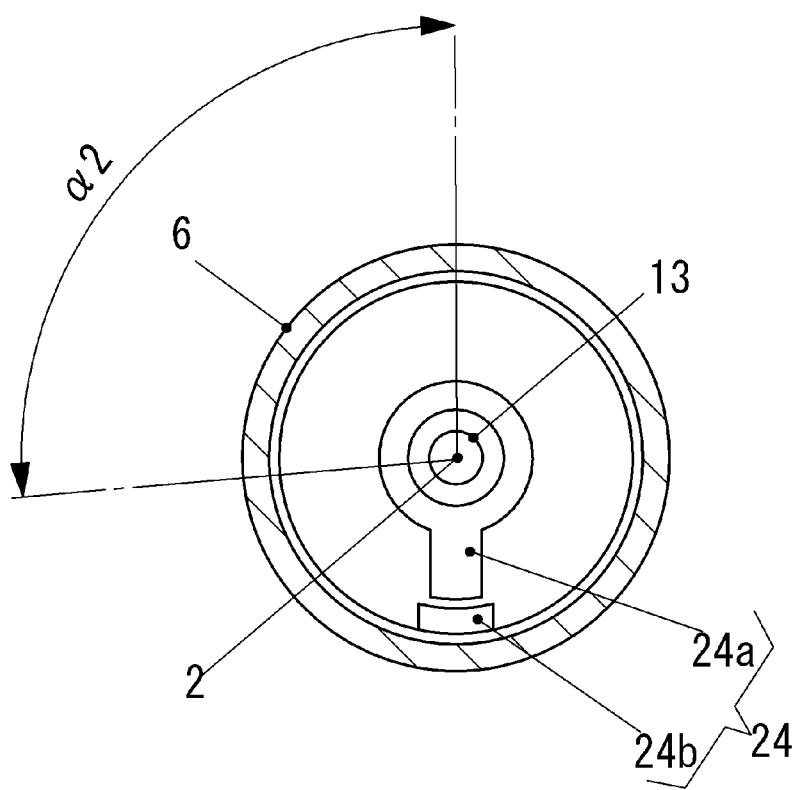
FIG. 3 is a diagram for a description of a pulse generator of a second motor of the probe for optical imaging.

FIGS. 1 to 3 illustrate the embodiment of the probe for optical imaging related to the invention.

FIG. 1 is a cross-sectional view of the probe for 3D scanning-type optical imaging related to the embodiment of the invention. A fixed side optical fiber 1 for guiding a light ray from a rear end side to a tip side of the probe is inserted into substantially a center inside a sufficiently long tube-shaped catheter 6.

A rotation side optical fiber 2 is rotatably provided on a tip side of the fixed side optical fiber 1. A first optical path conversion means 3 (which is indicated by reference numeral 3a or 3b according to positions in the drawing) including a prism having a shape formed by, for example, cutting both surfaces of a substantially columnar transparent body with a substantially nonparallel plane is rotatably attached to a tip of the rotation side optical fiber 2 independently of the rotation side optical fiber 2 by a first motor 12. When the first optical path conversion means 3 rotates, a light ray is rotated and emitted forward, for example, at an angle of θ1+θ2 with respect to an axial line in the drawing.

In addition, a second optical path conversion means 20, which concentrates a light ray penetrating the fixed side optical fiber 1 and rotates and emits the light ray toward the first optical path conversion means 3 at a minute angle (θ1) with respect to the axial line while being rotated, is attached to the tip of the rotation side optical fiber 2. Referring to FIG. 1, the second optical path conversion means 20 is formed by combining a conical condensing lens 20c and a prism 20a.

The rotation side optical fiber 2 and the fixed side optical fiber 1 are separated from each other at a minute distance of about 5 μm to face each other, and included in an optical rotary connector 22 together with a rotating douser 5 and an optical fiber fixture 4. End faces of the rotation side optical fiber 2 and the fixed side optical fiber 1 are smoothly processed. Further, a high transmittance may be maintained between the rotation side optical fiber 2 and the fixed side optical fiber 1, and the rotation side optical fiber 2 and the fixed side optical fiber 1 are optically connected to each other with little loss.

The first motor 12 is incorporated in the catheter 6, and a rotor magnet 11 is attached to the first motor 12. A hollow rotating shaft 10 supported on first bearings 9a and 9b rotates. In the first motor 12, a voltage is applied to a motor coil 7 through an electric wire 23, and the first optical path conversion means 3 is attached to a holder portion 10a of the hollow rotating shaft 10 and rotated.

In a second motor 19, a second rotating shaft 13 supported on second bearings 18a and 18b is lightly press-fitted to a hole formed substantially at a center of a vibrator 14, and stable frictional force is generated between the vibrator 14 and the second rotating shaft 13 due to elasticity or a characteristic of a spring of the vibrator 14. The second rotating shaft 13 of the second motor 19 fixes the rotation side optical fiber 2 in a center hole thereof, and voltages are applied to a pattern electrode 16 and an electrostrictive element 15 through a disposed electric wire 17, thereby rotating the second optical path conversion means 20. Rotation of the vibrator 14 is stopped with respect to a motor case 8. In the case of a simplest configuration, the electric wire 17 functions as a rotation stopper.

The first motor 12 is provided with a first pulse generating means 25 including a rotation member 25a and a fixation member 25b illustrated in FIG. 2, and the second motor 19 is provided with a second pulse generating means 24 including a rotation member 24a and a fixation member 24b illustrated in FIG. 3. The respective pulse generating means generate one or a plurality of pulse signals per rotation in response to rotations of the first and second motors. A magnetic sensor such as an induction coil, a Hall element, an optical sensor using an optical shutter and a light sensor, and the like, are used as a principle of generating pulses.

Referring to FIG. 1, in front of the first optical path conversion means 3 from which a light ray is emitted, a light-transmitting member 21 capable of transmitting the light ray is attached to the catheter 6 as necessary. A substantially spherical surface portion 21a is formed on the light-transmitting member 21 as necessary, and a thickness of the spherical surface portion 21a is changed rather than being constant under the necessity such that the spherical surface portion 21a has a function of a lens. The light-transmitting member 21 is made of a transparent resin, glass, or the like, and coated as necessary such that surface reflection is reduced, total reflection of the light ray is minimized, and transmittance is increased.

Figure 9:
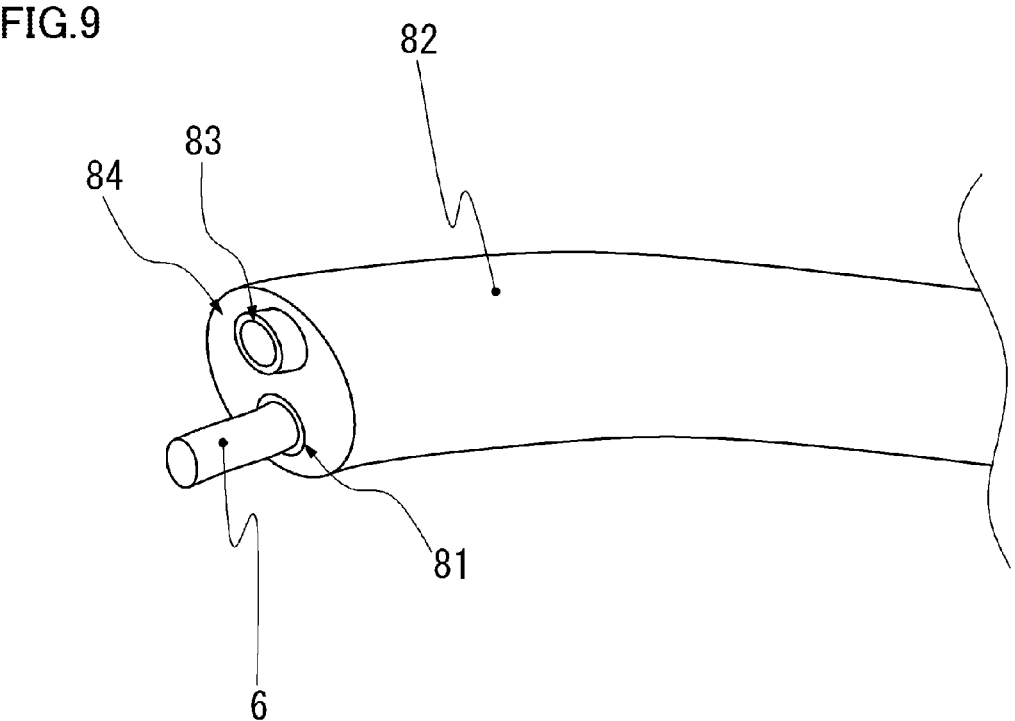
FIG. 9 is a diagram for a description of a guide catheter using the probe for optical imaging.

Referring to FIG. 9, a CCD camera unit 83 is attached to a distal end observation portion 84 of a guide catheter 82, and the tube-shaped catheter 6 is inserted into a through hole 81 referred to as a forceps channel.

Figure 10:
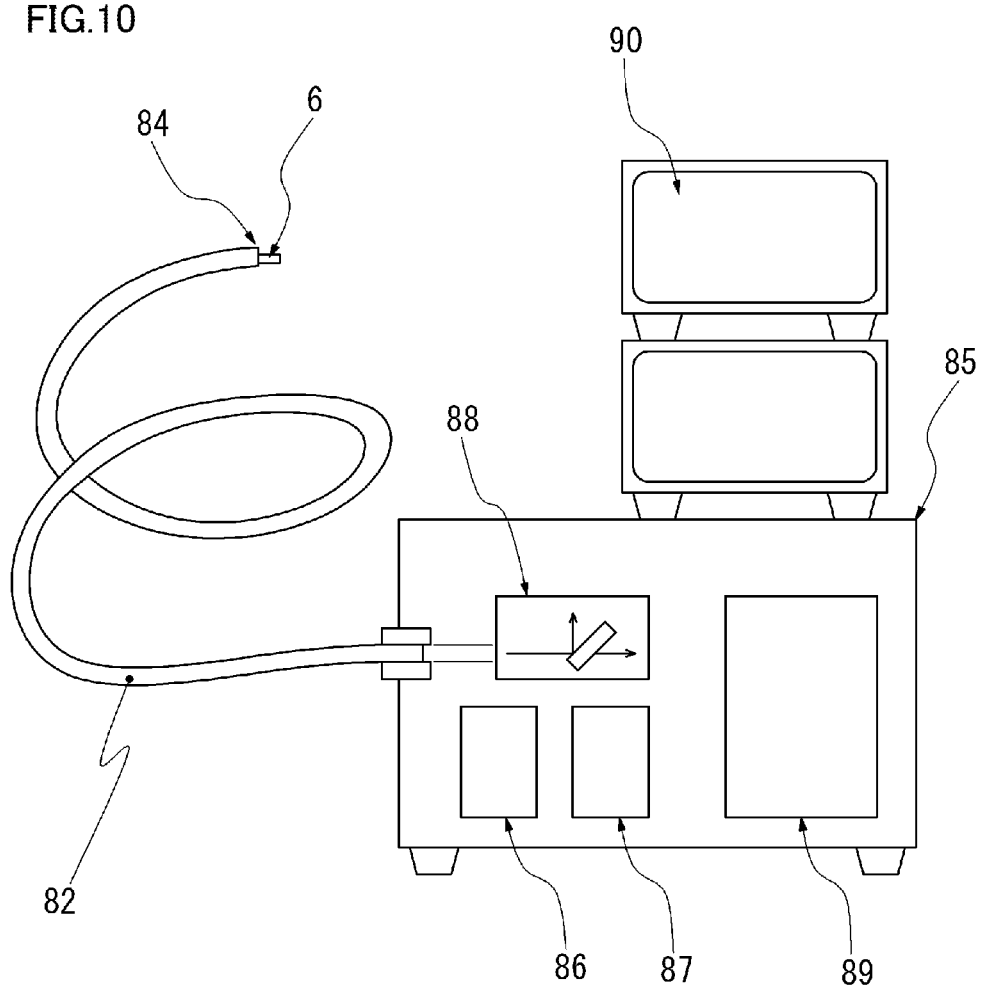
FIG. 10 is a diagram illustrating a configuration of an endoscope imaging apparatus using the probe for optical imaging.

The first motor 12 of FIG. 1 is driven and rotated by being supplied with power from a motor driver circuit 86 in a configuration of an endoscope imaging apparatus illustrated in FIG. 10, and the second motor 19 is driven and rotated by being supplied with a voltage from a second motor driver circuit 87. In addition, a rotation speed of the first motor 12 is adjusted by a pulse signal from the first pulse generating means 25, and a rotation speed of the second motor 19 may be adjusted to a predetermined value by a pulse signal from the second pulse generating means 24.

Next, a detail description will be given of characteristic effect of the probe for 3D scanning-type optical imaging of FIGS. 1 to 3 described above.

Referring to FIG. 10, a light ray such as far-red light, a laser beam generated from a light source in a main body 85 travels through the fixed side optical fiber 1 in the catheter 6 inside the guide catheter 82.

The light ray passes through the fixed side optical fiber 1 ⇒ the optical rotary connector 22, and is emitted to the rotation side optical fiber 2 ⇒ the second optical path conversion means 2 ⇒ the first optical path conversion means 3a. The light ray corresponding to the near infrared ray further passes through the light-transmitting part 21, and penetrates an outer layer of a skin of a test object up to a depth within a range of 2 to 5 mm. The light ray reflected therefrom is guided to an optical interference analyzer 88 in an opposite direction of the same optical path as that described above by passing through the light-transmitting part 21 ⇒ the first optical path conversion means 3a ⇒ the second optical path conversion means 20a ⇒ the rotation side optical fiber 2 the optical rotary connector 22 ⇒ the fixed side optical fiber 1.

Figure 12:
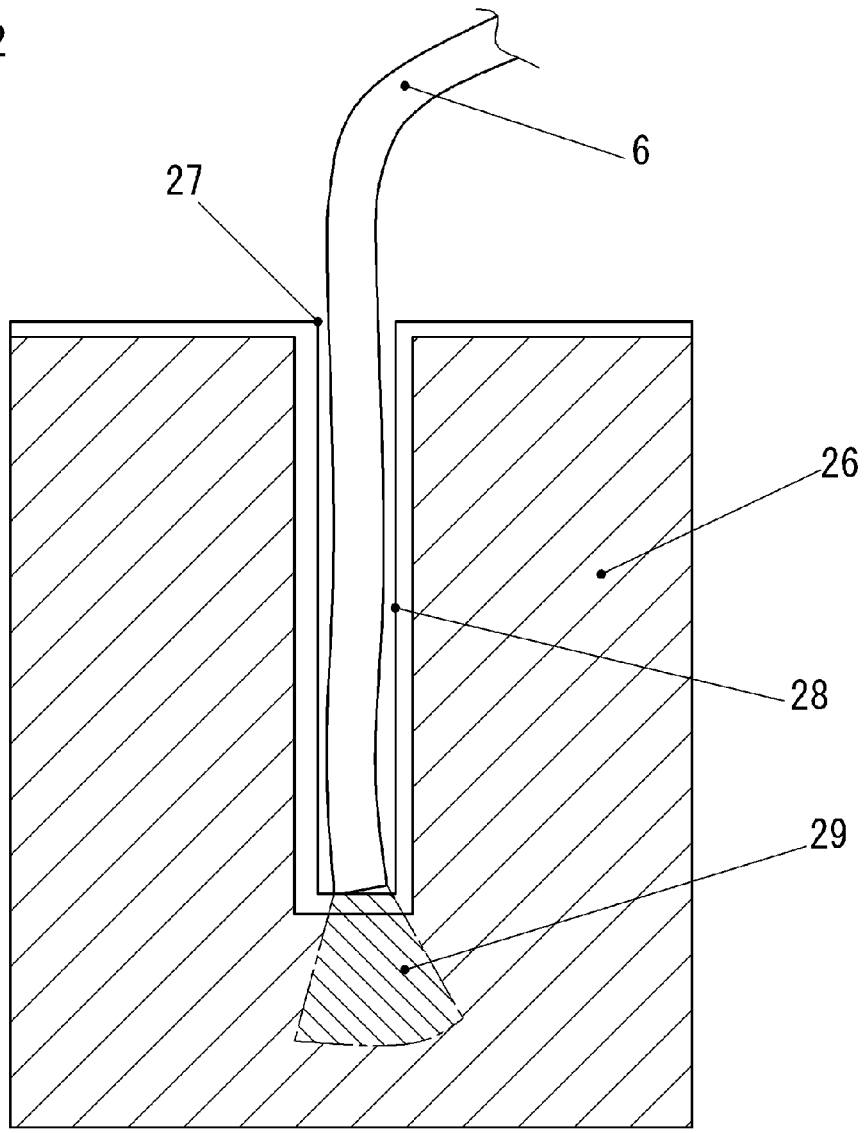
FIG. 12 is a diagram for a description of scanning of a deep hole by the probe for optical imaging.

Referring to FIG. 12, a thickness and presence/absence of an internal defect of a surface layer 27a are observed through a 3D image by emitting a light ray to an inner side of a deep hole 27 of a test object 26.

Referring to FIG. 1, even though power is supplied from the electric wire 23, and the first motor 12 rotates at a constant speed within a range of about 1,800 to 20,000 rpm, a guided light ray guided from the fixed side optical fiber 1 is emitted from the second optical path conversion means 20a by passing through the optical rotary connector 22 and the rotation side optical fiber 2, reflected from a substantially flat portion of the first optical path conversion means 3a, and rotated and emitted in a direction changed to a certain angular direction (a downward direction at an angle of θ1+θ2 indicated by an arrow in FIG. 1). In this instance, an angle α1 of the first pulse generating means 24 of the first motor 12 is 0°, and an angle of the second pulse generating means 24 of the second motor 22 is 0°. When a phase difference of the two angles is indicated by (α1−α2), the phase difference (α1−α2) becomes 0°.

In this state, an emission direction of the light ray is greatly curved with respect to an axial line, and an emission angle becomes a downward angle of (θ1+θ2).

Figure 4:
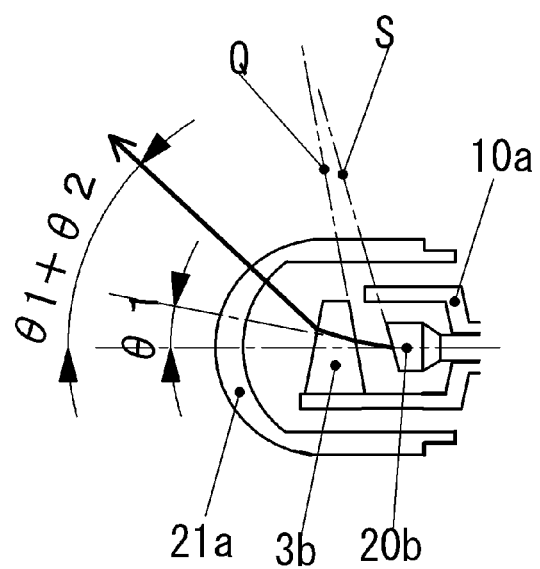
FIG. 4 is a diagram for a description of an operation of the probe for optical imaging.

Next, as illustrated in FIG. 4, when the first optical path conversion means 3 and the second optical path conversion means 20 rotate at the same rotation speed and shift to diametrically opposite positions to those of FIG. 1 corresponding to a first optical path conversion means 3b and a second optical path conversion means 20b, a light ray is emitted from the second optical path conversion means 20b, reflected from a substantially flat portion of the first optical path conversion means 3b, and rotated and emitted in a direction changed to a certain angular direction (an upward direction at an angle of θ1+θ2 indicated by an arrow in FIG. 4). In this instance, an angle α1 of the first pulse generating means 24 of the first motor 12 is 180°, and an angle of the second pulse generating means 24 of the second motor 22 is 180°. A phase difference (α1−α2) of the two angles is 0°, which is the same as that in FIG. 4. In this state, an emission direction of the light ray is greatly curved with respect to an axial line, and an emission angle becomes an upward angle of (θ1+θ2).

Referring to FIG. 4, an angle Q of the substantially flat portion of the first optical path conversion means 3b and an angle S of the surface of a prism 20d of the second optical path conversion means 20 should not be parallel to each other. For example, a difference between the angle Q of the substantially flat portion and the angle S of the prism 20d is 5° or more. If the substantially flat portion and the surface of the prism 20d are parallel to each other, a light ray may be totally reflected and an obtained OCD image may be degraded. When the first and second optical path conversion means are designed not to be parallel to each other in a state in which a phase difference (α1−α2) in rotation angle between the first and second optical path conversion means is 0°, there is no concern that the first and second optical path conversion means become parallel to each other in any state, and thus an excellent image is obtained.

Figure 5:
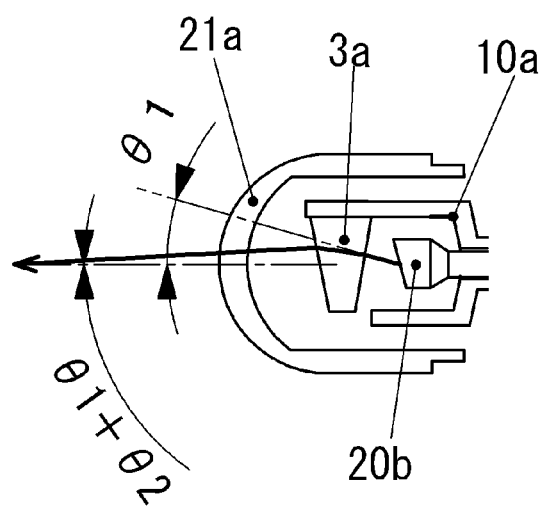
FIG. 5 is a diagram for a description of an operation of the probe for optical imaging.

Next, FIG. 5 illustrates a state in which a phase angle changes when rotation speeds of the first optical path conversion means 3a and the second optical path conversion means 20a are made different.

Referring to FIG. 5, a light ray emitted from the second optical path conversion means 20b with an angle with respect to an axial line is reflected from the substantially flat portion of the first optical path conversion means 3a, and a direction thereof is returned to a reverse angular direction. As a result, the light ray is rotated and emitted substantially on the axial line and substantially in parallel with the axial line. In this instance, an angle α1 of the first pulse generating means 24 of the first motor 12 is 0°, and an angle of the second pulse generating means 24 of the second motor 22 is −180° due to a delay in rotation. A phase difference (α1−α2) of the two angles is +180°. In this state, an emission direction of the light ray is (θ1+θ2)≈0°.

Figure 6:
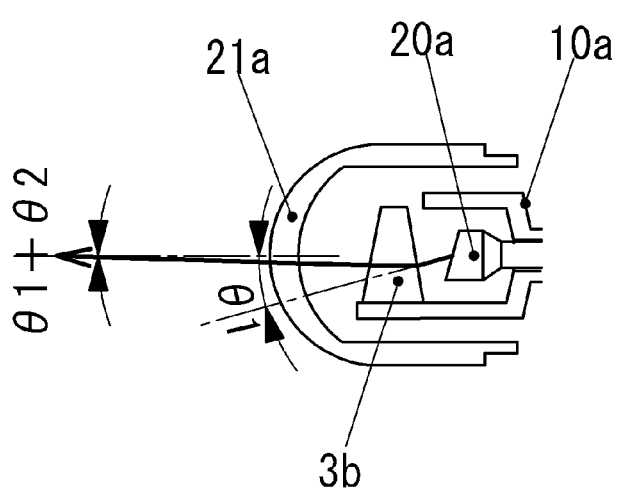
FIG. 6 is a diagram for a description of an operation of the probe for optical imaging.

Next, FIG. 6 illustrates a state in which the first optical path conversion means 3a and the second optical path conversion means 20a of the state of FIG. 5 are rotated up to diametrically opposite positions at the same revolutions per minute.

Referring to FIG. 6, a light ray emitted from the second optical path conversion means 20b with an angle with respect to the axial line is reflected from the substantially flat portion of the first optical path conversion means 3b, and a direction thereof is returned to a reverse angular direction. As a result, the light ray is rotated and emitted substantially on the axial line and substantially in parallel with the axial line. In this instance, an angle α1 of the first pulse generating means 24 of the first motor 12 is 180°, and an angle of the second pulse generating means 24 of the second motor 22 is 0° due to a delay in rotation. A phase difference (α1−α2) of the two angles is +180°. In this state, an emission direction of the light ray is θ1+θ2≈0° similarly to FIG. 6.

Figure 7:
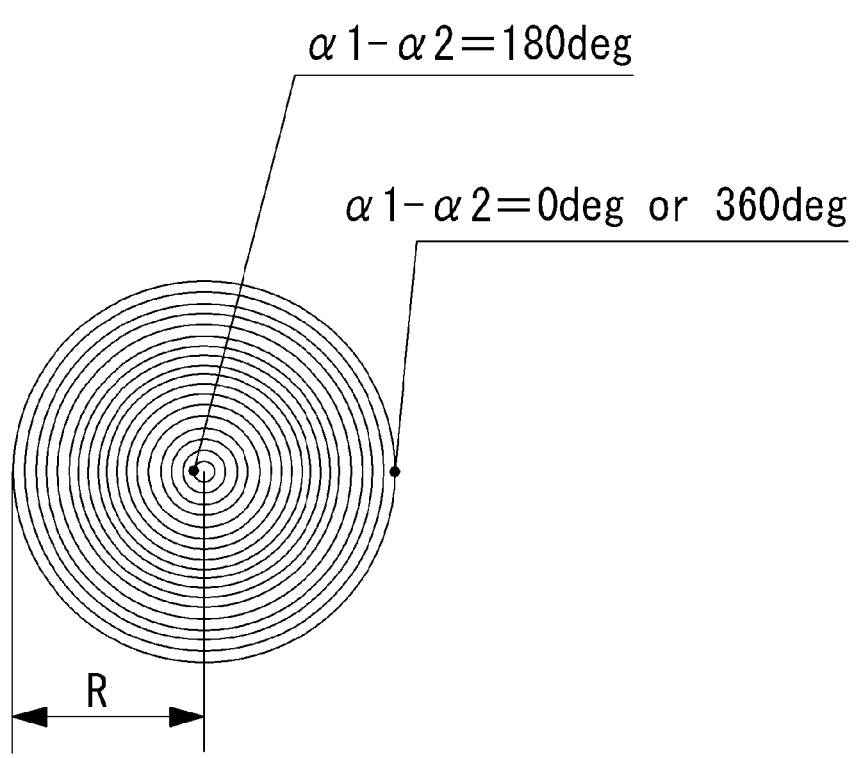
FIG. 7 is a diagram for a description of an emission range of the probe for optical imaging.

FIG. 7 illustrates rotation phase angles (α1−α2) described with reference to FIGS. 1 to 6, and an emission direction of a light ray corresponding to a forward direction. An emission direction changes due to a phase difference of (α1−α2) in an angle between the angle α1 of the first pulse generating means 24 of the first motor 12 and the angle α2 of the second pulse generating means 24 of the second motor 22, and the light ray is emitted in a range indicated by a radius R in the drawing rather than forward.

Figure 8:
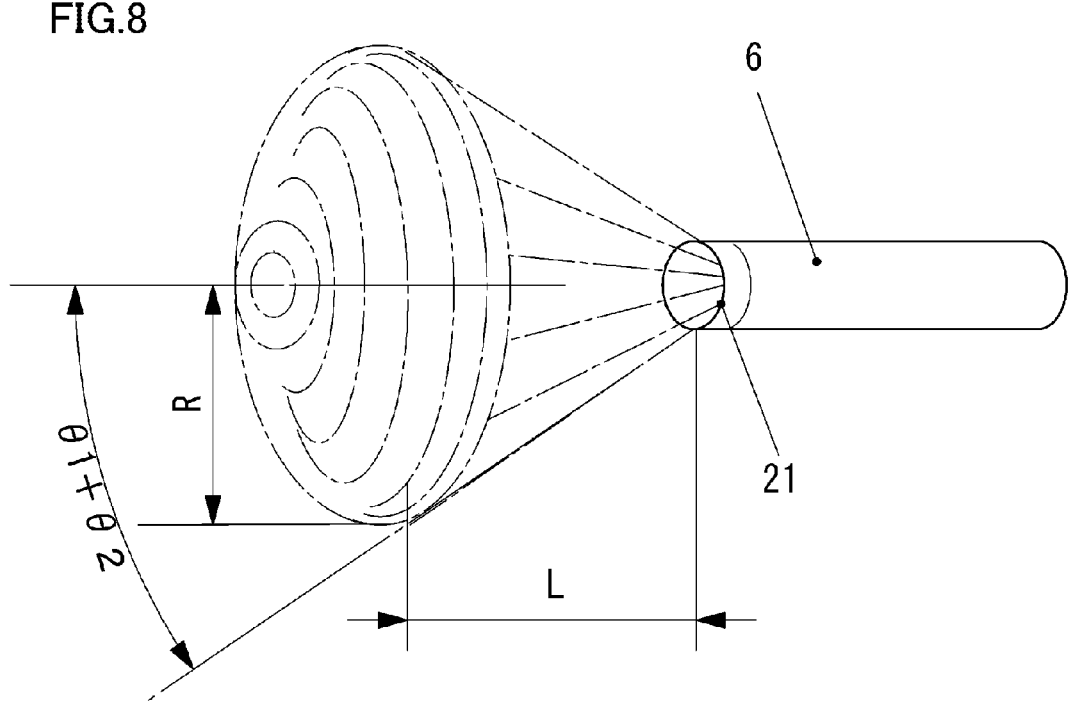
FIG. 8 is a diagram for a description of 3D scanning of the probe for optical imaging.

FIG. 8 is a diagram three-dimensionally illustrating an emission range of a light ray. The light ray is focused so as to be in focus in a range L in front of the catheter 6, and thus substantially conically emitted as indicated by an angle of (θ1+θ2) in a range of a radius R in the drawing, thereby three-dimensionally scanning a test object.

The light ray corresponding to the near infrared ray, the laser beam, or the like further passes through the light-transmitting part 21 of FIG. 1, and penetrates a surface of a test object up to a depth within a range of 2 to 5 mm. The light ray reflected therefrom is guided to the optical interference analyzer 88 through the light-transmitting part 21 ⇒ the first optical path conversion means 3 ⇒ the second optical path conversion means 20 ⇒ the rotation side optical fiber 2 ⇒ the optical rotary connector 22 ⇒ the fixed side optical fiber 1.

Figure 11:
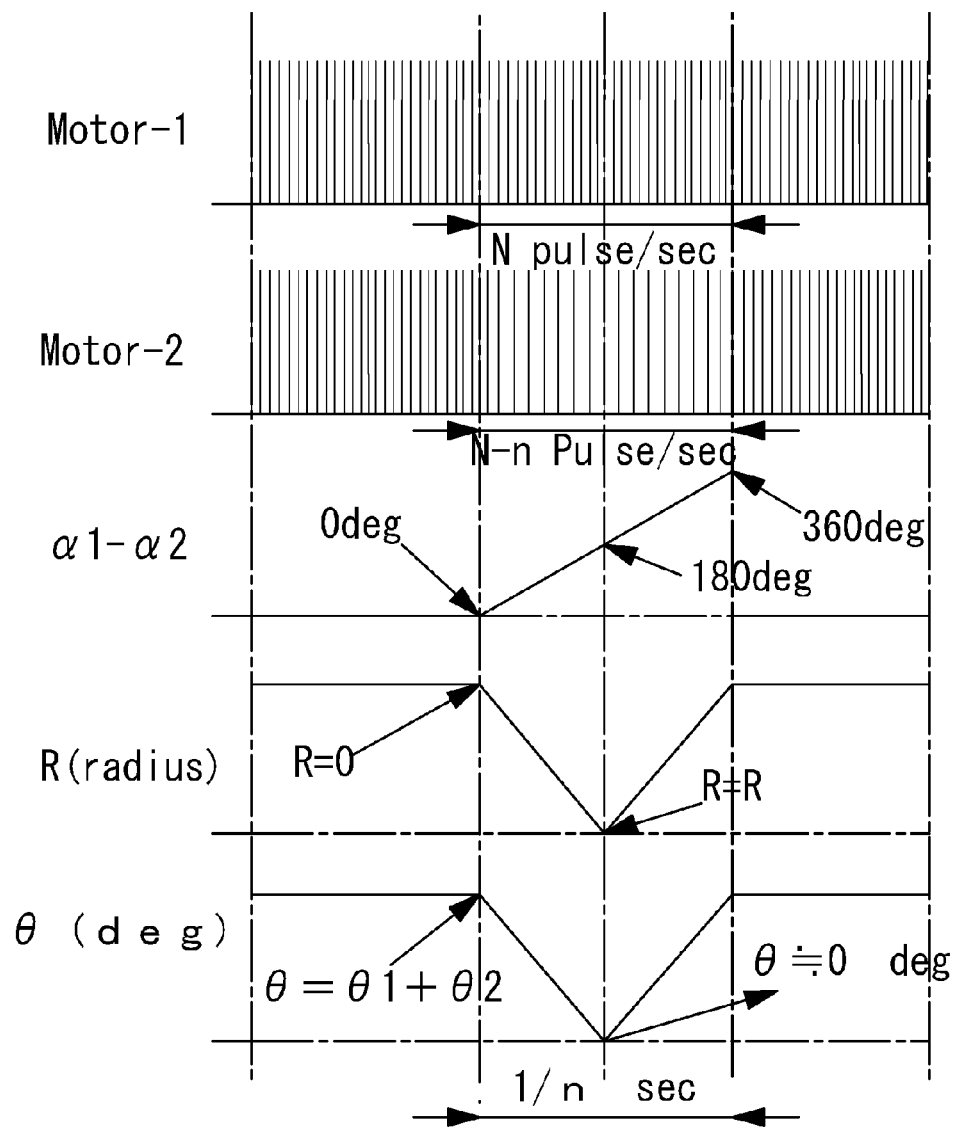
FIG. 11 is a timing chart illustrating an operation of the probe for optical imaging.

FIG. 11 illustrates timing charts of generated pulses of the first motor 12 and the second motor 19 of the probe for optical imaging according to the invention. The timing chart on the upper side of the drawing illustrates a pulse generated from the first pulse generating means 25 of the first motor 12, the timing chart on the lower side of the drawing illustrates a pulse generated from the second pulse generating means 24 of the second motor 19, and a horizontal axis indicates a time axis.

In the drawing, a time slot indicated by "stand by" corresponds to a state in which the first motor 12 and the second motor 19 have scanning start signals while rotating at the same revolutions per minute.

Next, in response to a start signal being output by an operation of a person who handles the probe for imaging, the first motor 12 rotates at a speed indicated by, for example, N pulses/second (for example, 30 rotations/second) and starts to store OCT observation image data of a test object in a computer 89.

At the same time, the second motor 19 rotates at a speed of (N−1) pulses/second (for example, 29 revolutions/second). Thus, as illustrated in FIG. 11, an emission angle changes from θ1 to θ2 for 0.5 second and returns to θ1 again after 1 second, thereby completing 3D emission of the light ray.

In this case, the computer fetches two 3D data in total (two data corresponds to 1 set) within a time period at which the emission angle reciprocates between α1 and α2, thereby obtaining a clear 3D OCT diagnosis image without missing. When data is fetched and stored, the first motor 12 and the second motor 19 are in a standby state again to rotate while waiting for a subsequent start signal.

A more practical method of using the OCT probe for 3D scanning of the invention is as follows. For example, in a first step, the OCT probe of the invention is sent into a long blood vessel. In this case, while the first motor 12 and the second motor 19 rotate at the same revolutions per minute, the OCT probe of the invention continuously performs 2D 360° scanning, thereby specifying a position of a diseased part near the blood vessel in the human body from a 2D image displayed on a monitor 90.

The 2D image is fetched using a pulse signal from the first pulse generating means 25, 25a, and 25b of FIG. 2 as a trigger, and displayed on the monitor 90 by computer processing.

Subsequently, in a second step, pushing and pulling of the OCT probe are suspended to stop the catheter 6, and the second motor 19 is rotated at a speed of, for example, (N−1) pulses/second (for example, 29 rotations/second) such that a light ray is three-dimensionally emitted. In this way, an OCT device may display a high-resolution 3D image on the monitor 90, thereby specifically observing the diseased part.

The 3D image is fetched to the computer 89 using, as a trigger, an instant at which both a pulse signal from the first pulse generating means 25, 25a, and 25b and a pulse signal from the second pulse generating means 24, 24a, and 24b illustrated in FIG. 3 are simultaneously output, and displayed on the monitor 90.

In a third step, the OCT probe of the invention is further moved to another end portion. In this case, while the first motor 12 and the second motor 19 rotate at the same revolutions per minute, the OCT probe of the invention continuously performs 2D scanning over a whole circumference of 360°. In this way, a 2D OCT image is displayed on the monitor 90.

In the present embodiment, on an inside over a whole length from a rear to a tip of the catheter 6, the fixed side optical fiber 1 is not rotated in the long catheter 6, and thus is not rubbed. Therefore, it is possible to prevent occurrences of rotation transmission delay, torque loss, and the like. In addition, the rotation side optical fiber 2 is rotatably disposed in the hole of the hollow rotating shaft 1, and sliding loss is not present. Thus, rotational irregularity of the motor 12 is significantly small. In a general evaluation scale, performance of a speed of revolution is indicated by a percentage of a rotation angle. In the invention, it is possible to achieve high performance of 0.01%.

On the other hand, referring to rotational irregularity of a conventional endoscope probe using a scheme in which an optical fiber is rubbed, poor performance of about 100 times or more thereof has been obtained.

FIG. 12 is a diagram for a description of scanning of a deep hole by the probe for optical imaging of the invention.

In a mechanical device, when the deep hole 27 is formed in the test object 26, and a surface thereof is covered with a surface layer 28, the catheter 6 enters the deep hole such that a coating thickness of the surface layer 28 may be measured, an internal organization may be three-dimensionally observed, and presence/absence of internal defect may be observed in a scanning range 29.

Figure 13:
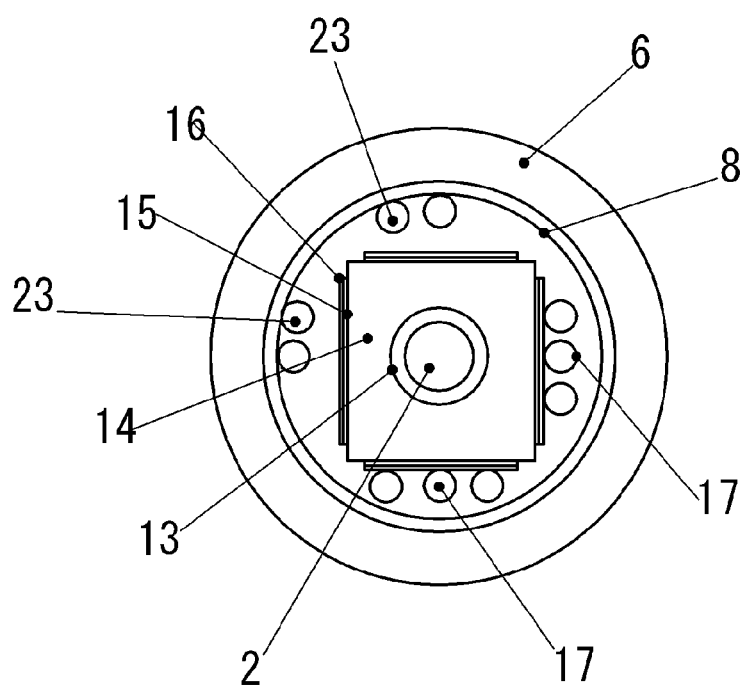
FIG. 13 is a cross-sectional view of the second motor of the probe for optical imaging.

FIG. 13 is a cross-sectional view of the second motor 19 of the probe for optical imaging.

A sufficient space is present between the vibrator 14 and the motor case 8 inside the catheter 6, and the electric wire 23 and the electric wire 17 are disposed in the space. In this way, wiring of the first motor 12 and the second motor 19 can be compactly performed with excellent space efficiency.

Figure 14:
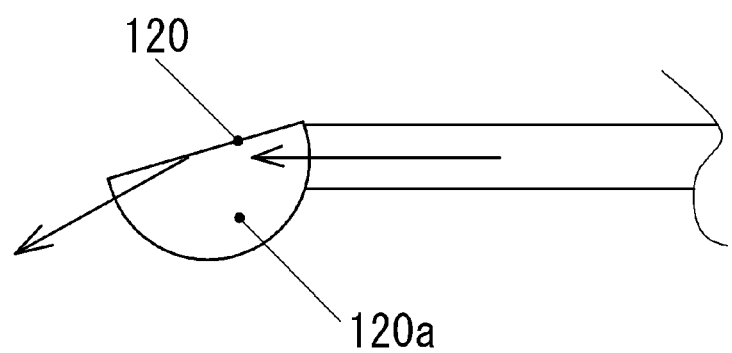
FIG. 14 is a diagram for a description of a modified application example of a second optical path conversion means of the probe for optical imaging.

FIG. 14 is a diagram for a description of a modified application example of the second optical path conversion means of the probe for optical imaging. The second optical path conversion means 120 is a prism having a substantially spherical surface 120a that inclines to a tip.

According to this configuration, the second optical path conversion means 120 may exhibit sufficiently high transmittance and condensing performance of a light ray, and thus it is possible to obtain a compact 3D observation image having high spatial resolving power.

FIG. 15 is a diagram for a description of a modified application example of the second optical path conversion means of the probe for optical imaging. The second optical path conversion means 220 includes a condensing lens 220c, a first prism 220d, and a second prism 220e, and is put in a cylindrical cover 220f.

According to this configuration, the second optical path conversion means 220 may incline a light ray at a sufficiently great angle, and thus it is possible to obtain a 3D observation image in a wide range.

Acquisition of a 3D image and enhancement of spatial resolving power of the 3D image are most importantly required performances in an OCT 3D operation image diagnosis apparatus of FIG. 10. Factors of enhancing spatial resolving power include rotation speed unevenness of the motor 12, runout accuracy of the hollow rotating shaft 10, accuracy and surface roughness of the first optical path conversion means 3 and the second optical path conversion means 20, and the like.

Among the factors, rotation speed unevenness of the motor 12 has great influence, and thus the endoscope probe of the invention that incorporates the motor 12 in the distal end portion and rotates an optical path conversion element at high accuracy and without rotation speed unevenness can stably achieve, for example, high 3D spatial resolving power of 10 μm or less.

According to the invention, an optical fiber is not relatively rotated in a catheter of an endoscope device, or the like, and thus is not rubbed, and occurrences of rotation transmission delay, torque loss, and the like are reduced, thereby obtaining a clear OCT analyzed image at high spatial resolving power of 10 μm or less. In addition, when a thickness of a second optical path conversion means is intentionally changed, a light ray may be emitted in a certain range in an axial direction, and thus a 3D observation image may be obtained.

INDUSTRIAL APPLICABILITY

A probe for 3D scanning-type optical imaging of the invention may improve spatial resolving power corresponding to basic performance of an OCT image diagnosis apparatus to have spatial resolving power of about 10 μm or less without rotating an optical fiber in a long tube by providing an optical path conversion means that is rotated without uneven speed by a motor near a tip of the tube, thereby having a high-accuracy rotary scanner. Furthermore, 3D observation of a bottom of a deep hole may be three-dimensionally scanning a front portion, and the probe may be applied to an OCT diagnosis apparatus for industrial use. In addition, the probe is expected to be used to diagnose or treat a minute seat of disease in a medical field.

EXPLANATIONS OF LETTERS OR NUMERALS

1 Fixed side optical fiber
2 Rotation side optical fiber
3, 3a, 3b First optical path conversion means (prism)
4 Optical fiber fixture
5 Douser
6 Catheter (tube)
7 Motor coil
8 Motor case
9a, 9b First bearing
10 Hollow rotating shaft
10a Holder portion
11 Rotor magnet
12 First motor
13 Second rotating shaft
14 Vibrator
15 Electrostrictive element
16 Pattern electrode
17, 23 Electric wire
18a, 18b Second bearing
19 Second motor
20, 20a, 20b, 120, 220 Second optical path conversion means
20c, 220c Condensing lens
20d, 120a, 220d, 220e Prism
21 Light-transmitting member
21a Spherical surface portion
22 Optical rotary connector
24, 24a, 24b Second pulse generating means
25, 25a, 25b First pulse generating means
26 Test object
27 Deep hole
28 Surface layer
29 Scanning range
81 Forceps channel
82 Guide catheter
83 CCD camera unit
84 Distal end observation portion
85 Main body
86 First motor driver circuit
87 Second motor driver circuit
88 Optical interference analyzer
89 Computer
90 Monitor
220f Cover

The invention claimed is:

1. A probe for optical imaging which guides light entering a tip side to a rear side, the probe comprising:
   a fixed side optical fiber non-rotatably disposed and incorporated in a substantially tube-shaped catheter;
   a first optical path conversion means disposed on a tip side of the fixed side optical fiber and driven and rotated by a first motor to rotate and emit a light ray forward at an angle inclined with respect to a rotation center;
   a rotation side optical fiber disposed between the fixed side optical fiber and the first optical path conversion means, optically connected by an optical rotary connector, and driven and rotated by a second motor; and
   a second optical path conversion means for rotating and emitting light to a tip side of the rotation side optical fiber by tilting an optical path by a minute angle with respect to a rotation center, and emitting a light ray toward the first optical path means,
   wherein the fixed side optical fiber, the first optical path conversion means, the rotation side optical fiber, and the second optical path conversion means are substantially collinearly disposed,
   wherein the light ray is emitted forward by penetrating the optical rotary connector, the second optical path conversion means, and the first optical path conversion means in order from the fixed side optical fiber.

2. The probe for optical imaging according to claim 1,
   wherein a rotating shaft of the first motor has a hollow shape, the first optical path conversion means is fixed thereto, and the rotation side optical fiber rotatably penetrates into a hollow hole, and
   a rotating shaft of the second motor has a hollow shape, and the rotation side optical fiber is fixed to a hole corresponding to the hollow shape and rotated.

3. The probe for optical imaging according to claim 1, wherein the first optical path conversion means is a rotatable prism.

4. The probe for optical imaging according to claim 1, wherein the second optical path conversion means is a prism having a substantially inclined flat surface at a tip.

5. The probe for optical imaging according to claim 1, further comprising:
   a first pulse generating means for generating at least one or more pulses per rotation according to a rotation angle of the first motor;
   a second pulse generating means for generating at least one or more pulses per rotation according to a rotation angle of the second motor; and
   a control means for adjusting rotation speeds of the first and the second motors by pulses from the first and second pulse generating means,
   wherein the light ray is emitted forward from the first optical path conversion means at a rotation speed of N1 [rotations/second] by setting a relation between a rotation speed N1 of the first motor and a rotation speed N2 of the second motor to N2=N1−X [rotations/second], and an emission angle of the light ray with respect to the rotation center is changed at a speed of X [reciprocations/second].

6. The probe for optical imaging according to claim 1, wherein a condensing lens, a first prism, and a second prism are substantially collinearly disposed in the second optical path conversion means.

7. The probe for optical imaging according to claim 1, wherein the rotatable prism and the substantially inclined flat surface at the tip of the prism of the second optical path conversion means are nonparallel to each other in the first optical path conversion means.

8. The probe for optical imaging according to claim 1, wherein the second optical path conversion means is a prism having a substantially spherical surface inclined to the tip or a ball lens having a reflecting surface corresponding to a substantially flat surface in a portion of a substantially hemispheric shape.

* * * * *